(12) United States Patent
Mayworm (10) Patent No.: US 9,940,004 B2
(45) Date of Patent: Apr. 10, 2018

(54) METHODS AND SYSTEMS FOR PREDICTING AND EVALUATING COFFEE CHARACTERISTICS

(71) Applicant: Gregory Mayworm, Libertyville, IL (US)

(72) Inventor: Gregory Mayworm, Libertyville, IL (US)

( * ) Notice: Subject to any disclaimer, the term of this patent is extended or adjusted under 35 U.S.C. 154(b) by 737 days.

(21) Appl. No.: 14/216,034

(22) Filed: Mar. 17, 2014

(65) Prior Publication Data

US 2014/0282198 A1  Sep. 18, 2014

Related U.S. Application Data

(60) Provisional application No. 61/792,183, filed on Mar. 15, 2013.

(51) Int. Cl.

| G06F 3/0484 | (2013.01) |
|---|---|
| A23F 5/26 | (2006.01) |
| A23F 5/24 | (2006.01) |
| G06F 3/0481 | (2013.01) |
| G06T 7/00 | (2017.01) |

(Continued)

(52) U.S. Cl.
CPC ..... G06F 3/04847 (2013.01); G01N 15/0227 (2013.01); G01N 33/14 (2013.01); G06F 3/04817 (2013.01); G06T 7/0004 (2013.01); *G06T 2207/30128* (2013.01)

(58) Field of Classification Search
CPC ...... A47J 31/057; A47J 31/002; A47J 31/007; A47J 31/42; A47J 31/0657; A47J 31/407; A47J 31/04; A47J 31/10; A47J 31/24; G06F 3/03847; G06F 3/04817; G01N 15/0277; G01N 33/14; G06T 57/0004; G06T 2207/30128; A23F 5/262; A23F 3/18; A23F 5/00; A23F 5/04; A23F 5/08; A23F 5/10; A23F 5/24

IPC ............ G06F 3/03847,3/04817; G01N 5/0277, 33/14; G06T 57/0004, 2207/30128

See application file for complete search history.

(56) References Cited

U.S. PATENT DOCUMENTS

| 5,207,148 A * | 5/1993 | Anderson | A47J 31/36 137/893 |
|---|---|---|---|
| 8,495,950 B2 * | 7/2013 | Fedele | A47J 31/002 99/299 |
| 9,326,634 B1 * | 5/2016 | Fedele | A47J 31/002 |

(Continued)

OTHER PUBLICATIONS

VST New Products Announcement, Dec. 8, 2012.*

(Continued)

*Primary Examiner* — Tadesse Hailu
(74) *Attorney, Agent, or Firm* — Quarles & Brady LLP (57) ABSTRACT

Methods and apparatuses for predicting characteristics of coffee using only a portable communications device having data processing capabilities and an embedded camera. Images of a comminuted substance are captured by the camera, with particle characteristics being quantified and entered into a data processor of the portable communications device. This information is combined with archived data such as known characteristics of ground coffee. The combined information is processed to predict the final characteristics of the brewed coffee. Predicted final characteristics may be displayed on a display of the portable communications device.

22 Claims, 8 Drawing Sheets

(51) Int. Cl.
*G01N 33/14* (2006.01)
*G01N 15/02* (2006.01)

(56) References Cited

U.S. PATENT DOCUMENTS

| | | | | |
|---|---|---|---|---|
| 2005/0097021 A1* | 5/2005 | Behr | ...................... | G01N 21/85 |
| | | | | 705/36 R |
| 2007/0068393 A1* | 3/2007 | Nosler | .................. | A47J 31/007 |
| | | | | 99/279 |
| 2010/0085560 A1* | 4/2010 | Fedele | .................... | A47J 31/00 |
| | | | | 356/134 |
| 2010/0086653 A1* | 4/2010 | Fedele | .................. | A47J 31/002 |
| | | | | 426/231 |
| 2011/0246091 A1* | 10/2011 | Fedele | ............... | G01N 21/4133 |
| | | | | 702/25 |
| 2011/0256273 A1* | 10/2011 | de Graaff | ................ | A47J 31/42 |
| | | | | 426/112 |
| 2013/0087050 A1* | 4/2013 | Studor | .................... | A47J 31/52 |
| | | | | 99/285 |
| 2014/0123306 A1* | 5/2014 | Jung | .................. | H04L 41/5054 |
| | | | | 726/27 |
| 2014/0241590 A1* | 8/2014 | Day, Jr. | .............. | G01N 15/0205 |
| | | | | 382/110 |
| 2014/0263780 A1* | 9/2014 | Day, Jr. | .................. | A47J 42/38 |
| | | | | 241/63 |

OTHER PUBLICATIONS

VST Inc., Voice Systems Technology Inc., Apr. 2010.*
Asma Redi Baleker, Raw Quality value Calssification of Ethiopian Coffee Using Image Processing Techniques: In the case of Wollega region, Nov. 2011, Addis Abeba.*

* cited by examiner

METHODS AND SYSTEMS FOR PREDICTING AND EVALUATING COFFEE CHARACTERISTICS

CROSS-REFERENCE TO RELATED APPLICATION

This application claims the benefit of priority under 35 USC 119(e) of the filing date of U.S. Provisional Application Ser. No. 61/792,183, filed Mar. 15, 2013, to which said application is incorporated herein by this reference.

FIELD OF THE INVENTION

The present invention relates to determining coffee characteristics, using stored data, computer instructions, and images of a comminuted solid by a portable communications device, using image analysis and data processing, all within the portable communications device.

BACKGROUND

Many useful fluids have been prepared by dispersing comminuted solids therein. Such fluids may have relatively great utility, if certain qualities or characteristics are present. These qualities or characteristics may be highly reliant upon the amount of the comminuted solid is present in the fluid, or how much of one or more critical components of the comminuted solid has been extracted therefrom and dispersed within the fluid.

In one example of the present disclosure, brewing coffee has been part of our culture for centuries. Today, there are three main methods of brewing coffee: gravitational percolation such as drip brewing, infusion through steeping such as a French press and pressurized percolation such as espresso. The common thread of all coffee brewing is the proper extraction of the coffee that produces the desired strength for personal taste or regional preferences. The "ideal" cup of coffee has the optimum balance of extraction and strength for a brew method and type of coffee.

It is generally agreed among the various coffee associations that the ideal coffee extraction should range from 18 percent to 22 percent. However, the recommended range for strength is 1.15 percent to 1.35 percent for the Specialty Coffee Association of America (SCAA), 1.20 percent to 1.45 percent for the Specialty Coffee Association of Europe (SCAE), and 1.30 percent to 1.55 percent for the Norwegian Coffee Association (NCA). These organizations confirm that coffee strength preferences are regional as well as personal.

Each of these organizations sponsor the "Golden Cup Award" to those coffee purveyors who have proven their ability to brew coffee to defined standards of quality. The SCAA defines five points of quality: (1) proper ratio of coffee to water, (2) proper grind, (3) proper equipment operation, (4) good water, and (5) clean equipment. In order to qualify for the Golden Cup Award, the coffee formula must fall between 92 grams and 120 grams of coffee for 1.9 liter of water, resulting in strength from 1.15 percent to 1.35 percent as the amount of total dissolved solids which is commonly represented as TDS percent. Each of these organizations publish a "Coffee Brewing Control Chart" that graphically parameterize extraction (solubles yield), strength percent (solubles concentration), and brew ratio (mass coffee to volume water). The chart assumes the brewing method is drip percolation with a constant absorption factor built into the formulas. The absorption factor relates to the amount of fluid that is retained in the coffee bed of grounds.

The Coffee Brewing Control Chart is referenced in U.S. Pat. No. 7,952,697, which is incorporated herein by reference. The Coffee Brewing Control Chart has served the industry well for several years but lacks the flexibility to adapt to alternative brewing methods. The Coffee Brewing Control Chart was developed using drip brewers and does not consider immersion or espresso type brewers. There are many types of brewer apparatus in existence and many of them would require a custom chart for proper coffee brewing to meet these standards.

There are additional essential elements to brewing good coffee. The coffee grind quality and size distribution will affect extraction and taste over brew time. Adjusting the grind size is the most effective way to control bitterness and astringency but is never mentioned in U.S. Pat. No. 7,952,697, nor used within the Coffee Brewing Control Chart. The brewing method or equipment must control contact time, water temperature and turbulence. The SCAA and industry leaders teach that "particle size dictates brew time" (Ephraim, D., 2010 Optimizing Brewed Coffee Quality through Proper Grinding. SCAA Event Lecture). For example, the fine grind of an espresso under pressure will require a much shorter contact time than a traditional automatic drip brewer that uses a coarse grind without pressure. However, brew time is not easily adjusted for the majority of brewing apparatus which have a fixed dispersion rate of hot water onto the coffee bed of grounds. The brewer temperature as the water is emerging onto the coffee bed should be between 92 to 96 degrees C., per the SCAA. Lower temperatures will not extract properly and will result in a weak brew. Higher temperatures result in an over-extraction and contribute to the astringency and/or bitterness of the coffee. Turbulence is the amount of mixing action or agitation used during the brewing cycle. Turbulence will also cause a temporary increase in coffee extraction and assist in creating a uniform dispersion of water around the coffee grounds. Each brewing method and equipment will have its own ideal brewing settings or recipes. This is the art of brewing and will determine the best values for each brewing parameter for each individual or regional preference and type of coffee.

Because coffee consists of over 98 percent water, the quality of the water will affect extraction rate and overall taste. Water quality must be controlled for accurate coffee brewing. There are ideal ranges of TDS (125 to 175 mg/l), hardness (1-7 gr), calcium (17-120 mg/l) and an absence of iron and chlorine. Dissolved solids actually contribute to good taste; so pure water is never used.

Another element that contributes to coffee brewing quality is the filtering medium. The choices will depend on the brewing equipment and method. Cloth filters were the first used and are still in use today. The most common are the micro-etched metal screens and paper filters. The amount of residue or sediment allowed to pass through the filter will affect the mouth feel of the coffee but may also become an irritant for some people.

Figure 1:
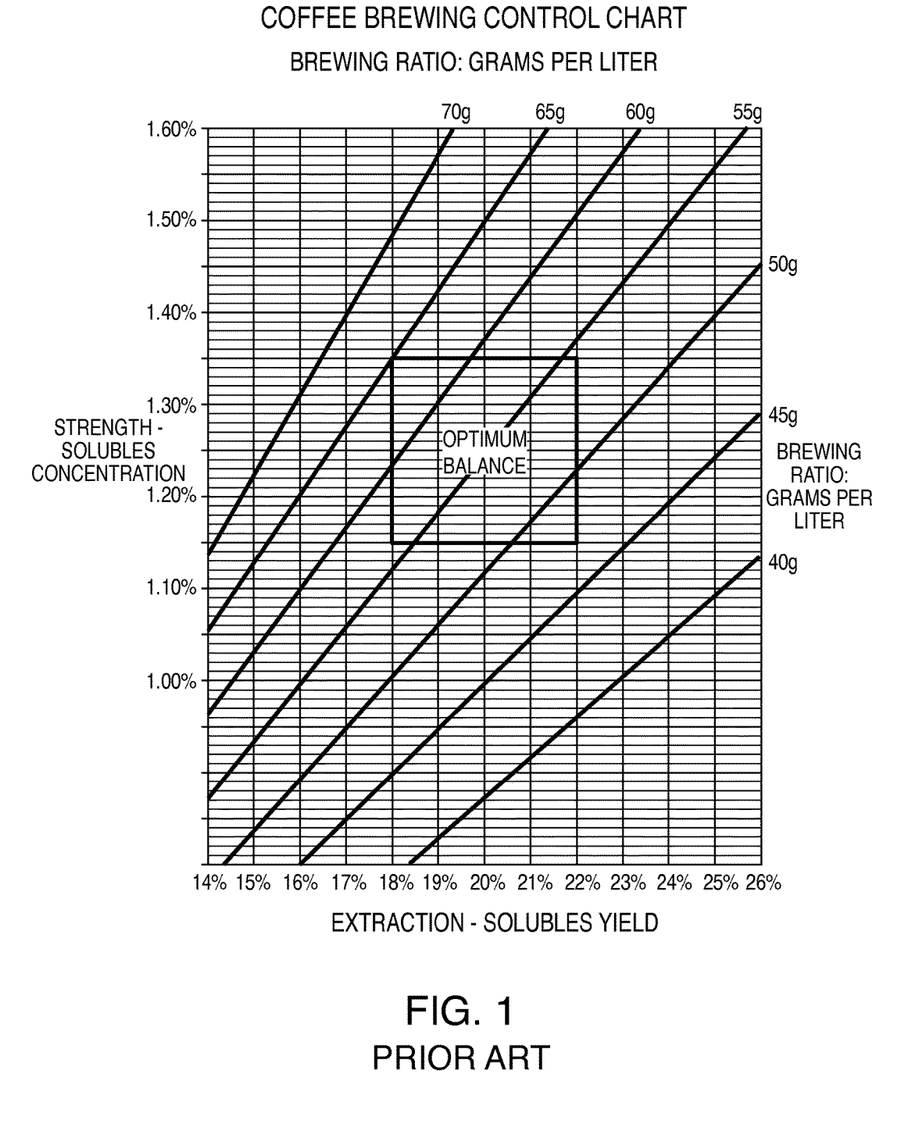
FIG. 1 is a prior art graph type chart depicting different coffee ratios, with strength plotted against extraction.

Brewing a superior cup of coffee requires control of more parameters than the three major ones described in the traditional Coffee Brewing Control Chart, such as that depicted in FIG. 1. A more comprehensive approach to determining the ideal brew ratio is needed that uses the mean coffee grind size as an input parameter as well as all the essential contributors to the coffee brewing method.

Coffee grind size distribution is critical in evaluating and determining coffee extraction characteristics. Coffee grinders are not calibrated to established standards and are adjusted to proprietary markings from fine to course. Without a known mean grind size, predictions of coffee extraction are inaccurate. Additionally, reproducing a coffee recipe accurately using different grinders is possible if the grinders are calibrated to each other. When the user can provide a measured average grind size, the coffee model's accuracy is greatly improved and as a result, its predictions of coffee extraction. Conventionally, coffee grind size or the particle profile is not often calculated due to expensive or labor intensive equipment. The three primary methods of determining particle size distributions are calibrated sieving trays, laser diffraction, and image analysis.

Coffee grind analysis may be performed using stacked screen sieves corresponding to U.S. standard sieves numbers 12, 16, 20 and 30. The sample is placed in the top sieve corresponding to the coarsest screen and covered. Normally, the sieve stack is placed on a mechanical shaker for 5 minutes and then each sieve weighed to determine the particle size profile. Laser diffraction is based on the principal that the intensity of the light scattered by a particle is directly proportional to the particle size. The laboratory equipment used for laser diffraction is bulky and very expensive besides having inaccuracies when measuring non-spherical particles such as coffee grounds. Computer image analysis offers very accurate representation of irregular shaped objects that are clearly delineated from the image's background or other particles. Dispersing the particles without overlap is the primary challenge using this technique.

Reducing coffee "fines" to an acceptable level is critical for eliminating over extracted coffee which results in bitter taste. This, along with a graphical representation of grind distribution, is extremely important in conveying a coffee taste profile from cupping the same coffee within distribution channels.

There remains a need in the prior art for improved ways of modeling the characteristics of brewed coffee.

SUMMARY OF THE INVENTION

The methods and apparatus embodied and described herein use particle size distribution as the basis for calculations of coffee characteristics and adjustments to equipment for preparing coffee. In one aspect of the disclosure, image analysis tailored for coffee grind characteristics and designed for use on and entirely is contained within a portable communications device having an onboard camera. In another aspect of the disclosure, there is presented a computer application for utilizing particle size distribution to make predictions of coffee characteristics, and as the basis of steps of preparing coffee as a beverage.

Particle size distribution of ground coffee is particularly significant to subsequent coffee characteristics of the final beverage. Using average particle size as a controllable aspect of coffee brewing for a plurality of brewer apparatus has not been applied in the prior art. Particle size distribution, as that relates to how many particles are of what sizes, results in a better model for determining characteristics such as extraction, brew strength and potential taste profiles.

Where images are captured by a camera, the onboard camera of a smartphone or similar device, such as a laptop computer, is used to capture an image of the coffee grinds which is then fed to the image analysis module. A program loaded into the smartphone, hereinafter referred to as the application, uses inputs from a slider widget such as the grind setting, ranging from fine to coarse, to calculate the brew ratio. After completing the coffee grind analysis, the application displays the recommended setting for that particular grind size configuration. The user may also import a stored image from the photo gallery for coffee grind analysis if it meets the application specifications. The specifications delineate how the sample is collected and dispersed on a pre-formatted collection card with measurement markers. These markers are detected by the application to correctly set the image scale.

The application uses its image analysis tool to check the quality of the grinder and point out performance issues or warn when coffee "fines" are at an unacceptable level. The coffee grind analysis tool within the application will not only help with the coffee model, but serve as a monitor of coffee grinder performance. Maintenance and recalibration of the grinder will be easier with the grind analysis tool of the application. In addition, knowing the grind distribution eliminates a variable that has plagued the industry when trying to accurately duplicate a coffee recipe.

Accordingly, to meet the needs described above, the present disclosure provides a predictive method of determining coffee strength based on a coffee model that incorporates the primary parameters that affect coffee extraction, notably, grind profile, brew time, brew temperature and turbulence for a given brew method and type of coffee. The predictive accuracy of the coffee strength requires a calibrated water source and a mean grind size to be established. The method and system disclosed herein use image analysis of a calibrated photo of dispersed coffee grinds to provide a particle profile with mean grind diameter. This value may then be entered into the coffee calculator panel to predict the coffee extraction. Users such as consumers will have an easy way to calculate brew ratios using a variety of measurement preferences such as by volume or weight. Even with limited knowledge of the brewing process and chemistry, users have tangible slider widgets that go from weaker to stronger for strength and fine to coarse for grind. Professionals can perform a complete coffee grind analysis using the particle analysis system and method. They are able to dial in the coffee input parameters using the additional supplied TDS percent widget as well as the coffee grind size widget specified as a diameter. Setting the brewer may be as simple as selecting a preconfigured brewer or inputting a new brewer with custom brewing parameters. The application is adaptable to a variety of brewing methods and solves the inherent problems with the industry standard Coffee Brewing Control Chart. The Coffee Brewing Control Chart was designed for drip percolator brewers and does not correctly predict the extraction for immersion type brewers or espresso machines. The chart is also very difficult to interpret being reproduced in many different measurement systems and by the fact that measuring water by volume is temperature dependent and difficult to do accurately. This novel application will do multiple conversions and adjust water volumes based on temperature if requested, but it is recommended to do all coffee ratio measurements by weight to improve accuracy. It also introduces a new way to approach coffee brewing based on grind size and is not limited to the "particle size dictates brew time" which is a current industry teaching.

The coffee model will improve over time due to accumulating user ratings and preferences with measured results. The application allows the user to rate each brew which will be stored within the database storage and may be shared to the cloud for global trending and analysis. The global cloud storage can be used for collective intelligence that recommends coffee beans and products that match the user's likes or dislikes.

The data collected from the application is compared to the coffee brews that are rated and those that have the TDS percentage measured using alternative test methods. The TDS percentage may be reported by using one of the following measurements methods, including TDS meter (conductivity), refractometer (brix), oven dehydration, and hydrometer.

The methods and systems disclosed herein advance the state-of-art due to incorporating all the major coffee brewing parameters that influence coffee taste. In addition, global cloud storage is used with collective intelligence methods for recommendations and trends within specified geolocations. The rating system provides methods for qualifying users and several levels of rating permissions. Professional coffee cuppers have access to the complete rating system while consumers will need to prove their expertise before gaining access to these advanced features. The coffee particle grind analysis tool provides a powerful tool accessible on a smartphone or mobile computer for in-field operations.

Moreover, methods and systems described herein and the associated application allows for assessment of different brewers and grinders, thereby producing accurate comparisons between different brewers and grinders.

Further, the application discloses a method for determining a coffee brew ratio utilizing a coffee extraction model that is configurable for a plurality of brewing apparatus, comprising: selecting a brewing method configured for said brewing apparatus that includes extraction parameters of said coffee extraction model; particle analysis means for determining the average grind size of the coffee grounds used in said coffee extraction model that is proportional to the average surface area of the coffee grounds; and, computing the brew ratio given said average grind size and an adjustable desired coffee strength, which is equivalent to the percent of dissolved solids within the brewed coffee; whereby, the coffee brew ratio is displayed in a human readable form as an amount of coffee and an amount of water with a plurality of measurement units.

The application also discloses a machine for determining the coffee brew ratio that results from a selected coffee brew strength using a plurality of brewing apparatus, comprising: a computer or derivative of, such as a tablet or a smartphone, which provides the framework for hosting the software application; a non-volatile memory in said computer that stores said software application that can be launched to begin execution and linked to associated databases; a user interface generated from said software application and presented on the computer display screen; an input device used to navigate said user interface in a plurality of form factors including but not limited to a touch screen or mechanical mouse; a plurality of widgets attached to said user interface that allow setting of values to be stored in said memory and/or database for use by a coffee extraction model that computes said coffee brew ratio; a particle analysis means for determining the average grind size of the coffee grounds used in said coffee extraction model that is proportional to the average surface area of the sample coffee grounds; and, a grind size widget that is attached to said user interface that inputs said average grind size that is stored in said memory and accessed by said coffee extraction model; whereby, the coffee brew ratio is displayed in a human readable form as an amount of coffee and an amount of water with a plurality of measurement units.

It is an object of the invention to provide improved elements and arrangements thereof by apparatus for the purposes described which is inexpensive, dependable, and fully effective in accomplishing its intended purposes.

These and other objects of the present invention will become readily apparent upon further review of the following specification and drawings.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION

Referring first to FIG. 1, there is shown a standard industry chart which indicates an optimum balance or combination of solubles concentration and solubles yield when preparing coffee from ground coffee beans. The central section of the chart indicates a combination widely held to produce a superior tasting coffee. The coffee strength is the primary qualifier for the overall taste and is represented on the vertical axis as percentage of total dissolved solids (TDS %). The center of the "Optimum Balance" region in the chart is centered at 1.25% TDS. Whereas this chart may be consulted in manual and other conventional ways to calculate an optimum balance for professional and amateur brewers of coffee, it must be utilized in combination with other apparatuses, such as calculators, data processors, and the like.

Figure 2:
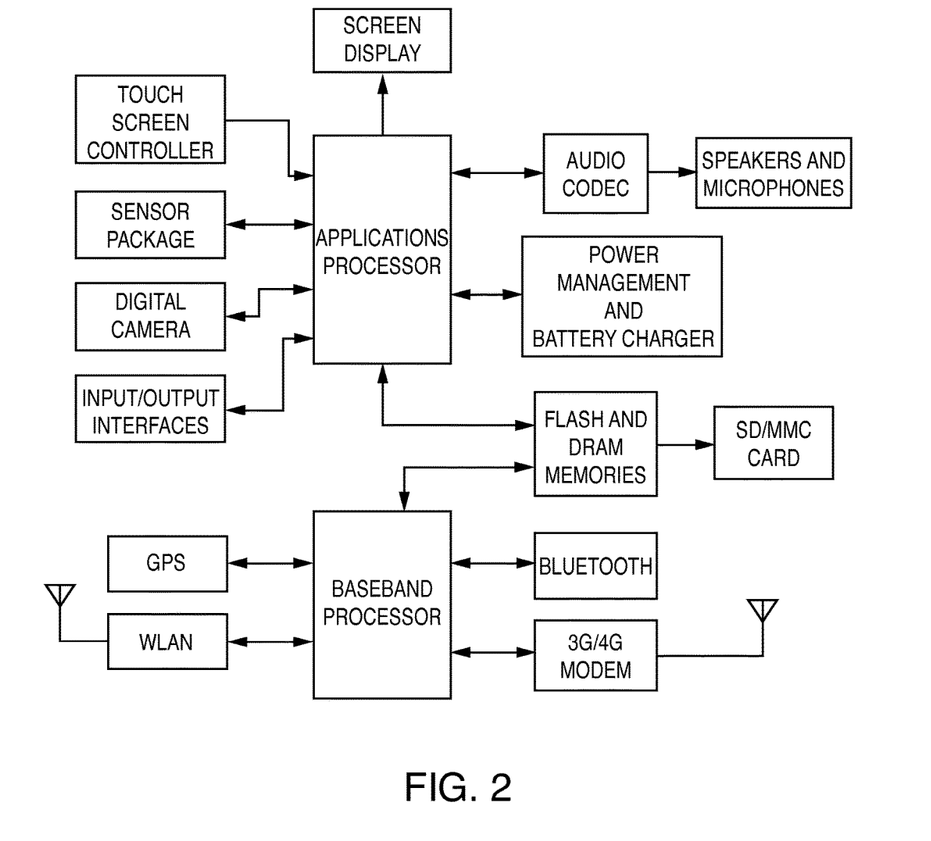
FIG. 2 is a block diagram of components of a portable communications device such as a smartphone or tablet computer.

By contrast with the prior art approach summarized above, the present invention sets forth a fully self-contained system in the form of a hand carried, portable communications device, such as a smartphone. According to the present disclosure, a smartphone including a camera may be loaded with an application which enables the entire process of calculating and predicting coffee characteristics to be conducted using only the smartphone and a sample of ground coffee (not shown). FIG. 2 shows components which may be present in a suitable smart phone (not shown in its entirety).

While the present invention is described in terms of the smartphone represented in FIG. 2, it should be understood that systems and methods according to the present disclosure are not limited to smartphones. Illustratively, these systems and methods may be implemented as a tablet computer, a web application or a computer program. The advantages of using a smartphone are the convenience of a mobile platform with a powerful applications processor, an embedded digital camera, sensor packages and access to wireless technology. These advantages enable systems and methods described below to be implemented entirely within a smartphone or tablet computer. A coffee brewing simulator and particle analyzer are well suited to the capabilities of a modern smartphone or tablet computer as shown in FIG. 2.

Figure 3A:
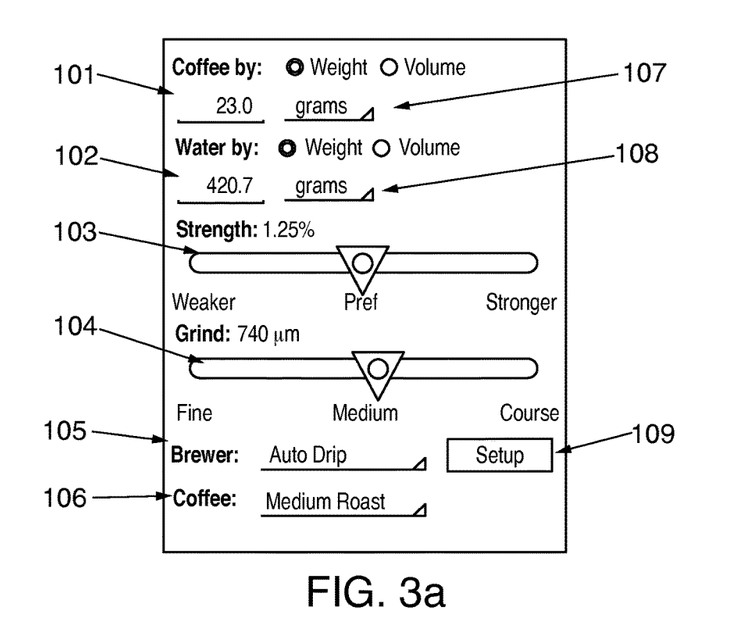
FIG. 3a is a depiction of a screen which may be displayed on the portable communications device of FIG. 2, the display showing a representative coffee calculation activity.

An application which generates a display seen in FIG. 3a may be loaded into the smart phone to result in a calculator, or an adaptable coffee model, that predicts the coffee extraction yield before the brewing process has begun. The user first determines whether the focus is to specify the amount of coffee by selecting a weight of ground coffee 101 or by selecting the amount of water to be used by selecting 102. The selected focus (101 or 102) may be highlighted, such as with color underlines. The user has options 107 to specify by weight or volume for coffee as well as measuring units. The user has options 108 to specify by weight or volume for water as well as measuring units.

A virtual slider bar 103, is a widget operable by finger motion on the screen of the smartphone, is set to the user's preference which in this case (referring to the chart shown in FIG. 1) is illustrated at 1.25%. As the slider bar is moved between Weaker and Stronger the unfocused amount (101 or 102) is immediately updated.

Coffee grind will affect the extraction yield linearly as a function of particle surface area (Zanoni D, 1991 Modeling the Aqueous Extraction of Soluble Substances from Ground Roasted Coffee. J Sci Food Agric 1992, 58, 275-279). The mean particle distribution density of coffee grinds can be assigned an overall grind diameter that relates to the particle surface area. This is the value that should be entered into 104 using the Grind slider bar.

The brewer setup parameters are configured using a virtual key 109 or selected using the drop-down list in an option indicated as 105. Brewers can be added and deleted using a setup button 109 which brings up a brewer settings screen shown in FIG. 3b. Each of the settings must be configured for each brewer so that the coffee model has the necessary values in calculating the extraction yield. The user has three options (seen as 118 in FIG. 3b) to delete, create or save brewer settings.

Continuing to refer to FIG. 3a, the coffee roast level is selected using a drop-down list seen at 106. Five different levels of roast will further adjust the coffee extraction model for more accurate predictions.

The user interface shown in FIG. 3a is implemented with a native application framework using a programming language. Which programming language is used does not materially affect the application design which may be described by a top-level flow diagram.

Figure 4:
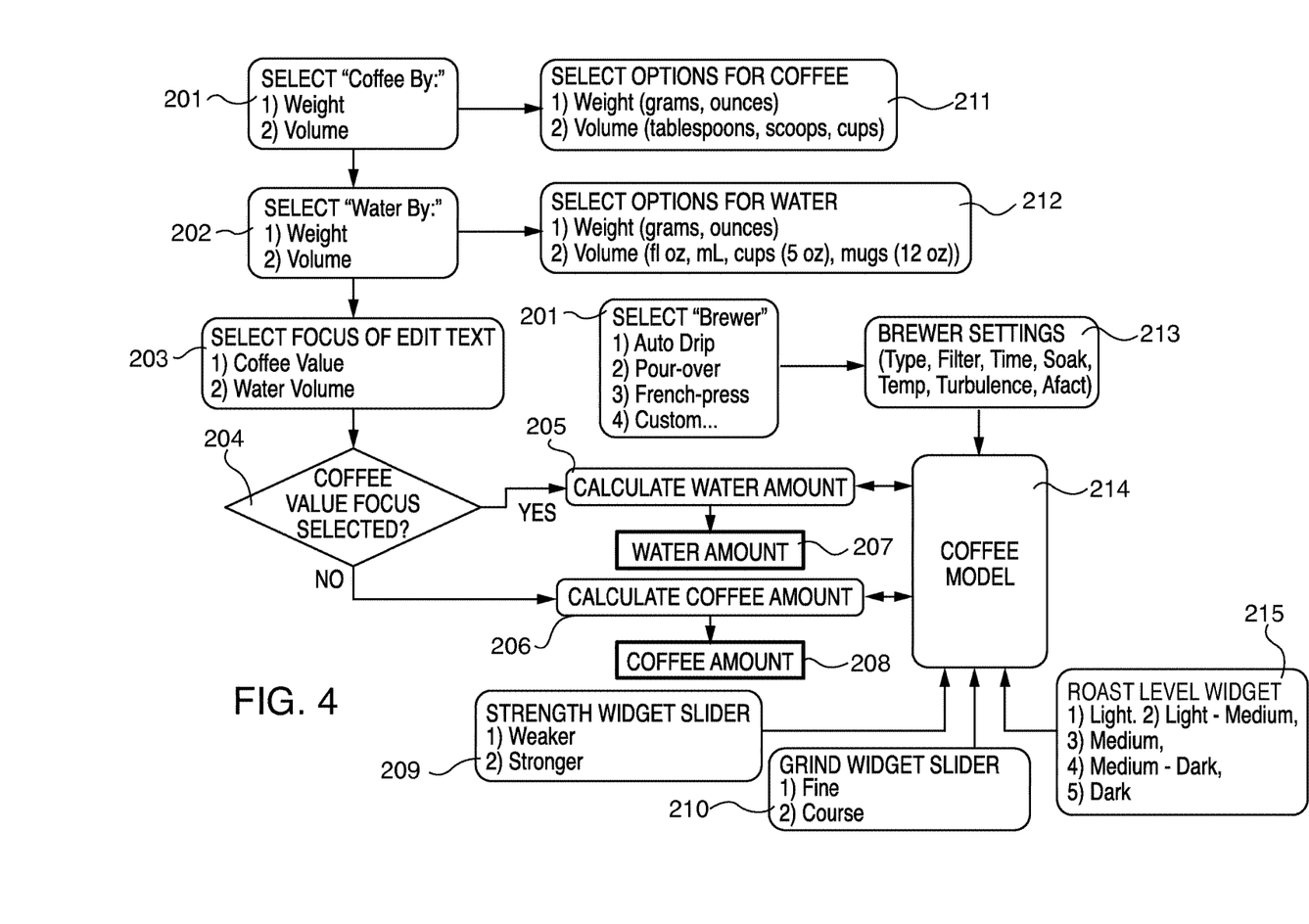
FIG. 4 is a flowchart of a process of determining brew strength when preparing a coffee beverage.

FIG. 4 describes a brew strength flow diagram presented on a screen generated by the application, which may correspond to the user interface shown in FIG. 3a. As previously described, the user begins by selecting the focus of the calculation at either a choice between weight and volume of ground coffee 201 or a choice between weight and volume of water 202, with the preferred approach of the calculation being selected at 203. Both of these options also allow the user to select the units for the calculations, seen at selection choices 211 or 212. The decision tree branches at 204 based on the previous selected focus. The application will either calculate the water amount at 205 or the coffee amount at 206. If the coffee amount has been selected, the coffee model 214 takes the input value from the focus amount and calculates the complimentary amount based on all the input parameters 213, 209, 210 and 215. These input parameters are manually selected by the user, who enters his or her choices on a widget, such as a virtual slider, presented within a graphic user interface on the screen of the smartphone. It will be understood that the graphic user interface's virtual widgets and prompts may be employed for all decisions to be made by the user.

The brewer type is selected at 201 which has configuration setting in 213. The brewers and brewer settings are configurable by the user to define their characteristics. The user also selects the desired coffee strength at 209, the coffee grind size at 210 and the roast level at 215. This completes the brewer assistance graphic user interface for selection procedures. The coffee model 214 is described in the following paragraphs.

Coffee brewing is similar to many other solid-liquid extractions. Studies have shown that extraction yield increases with temperature and decreasing particle size, whereas it decreases with increasing coffee/water ratio and degree of roasting (Voilley D., 1981 Diffusion of Soluble Substances during Brewing Coffee. J Food Pres 5 127-137, Spiro M. 1984 The Kinetics and Mechanism of Caffeine Infusion from Coffee: hydrodynamic aspects. J Sci Food Agric 35 925-930). The models for extraction kinetics are mostly base on Fick's law of diffusion but have been noted not to fit well with experimental data. Literature has shown linear correlation between average external surface area of the grounds and the variation of extraction yield over time. The average external surface area is calculated using the following relationship (formula 1):

$$A_{sp} = \frac{3}{\rho r}$$

where: $A_{sp}$=average external surface area (m$^2$ kg$^{-1}$) and $\rho$=coffee grounds bulk density (kg m$^{-3}$) and r is the radius.

Experimental data has shown the following relationship according to Zanoni, (formula 2):

$$EY_0 = 18.5 + \frac{.261}{\rho r}$$

where: $EY_0$=initial extraction yield at time zero. Formula (2) shows that the initial extraction is linearly related to the radius (or diameter) of the grounds. Once $EY_0$ is calculated, the $EY_\infty$ is calculated from the following relationship according to Zanoni (formula 3):

$$EY_\infty = 1.11 \times EY_0$$

where: $EY_\infty$ is the maximum asymptotic extraction yield. $EY_0$ may also be estimated based on the coffee particle distribution that decreases linearly with mean diameter as shown below (formula 4):

$$EY_0 = EY_\infty - kd$$

where: k is the grind constant and d is the mean diameter in micrometers.

The extraction yield EY can be modeled as a two-step process; the initial washing and then diffusion. Zanoni estimated this process with the relationship (formula 5):

$$EY = EY_0 + (EY_\infty - EY_0)(1 - e^{-kt})$$

where: EY is the extraction yield over time, k and t determine the rate constant.

These extraction equations are meant to show the general relationships but may be implemented with similar approximations (i.e. exponential, polynomial, etc.). Adjustments to the model should be looked at as refinements and are expected as the database becomes populated with coffee ratings and additional laboratory testing.

The study from which formula (4) was proposed used a constant brew temperature of 90 degrees C. A representative chart (CBC, 1955 Extraction Rates for Soluble Solids in Coffee Brew 47), demonstrates how extraction is affected by brew temperature. An approximation of the temperature effect based on the chart data can be expressed as (formula 6)

$$\text{percent Extractable} \propto 0.27T,$$

where: T is the temperature in Celsius. Not only does the temperature effect the extraction, it also has been shown to influence the coffee taste (ICO Quality Series, Chemical Changes Resulting from Variations in Temperature. Report No. 9). Expressed in terms of sensory evaluation, both acidity and body increase with higher brew temperatures and bitterness and astringency decrease with lower temperatures. The SCAA recommends a brewing temperature within the range of 92 to 96 degrees C.

Turbulence causes the coffee particles to separate allowing a uniform flow of water around them for proper extraction. The effect of turbulence on extraction is negligible (Spiro) and is modeled as a temporary increase in extraction. Turbulence is specified as an integer from 0 to 5 within the novel application and will contribute an amount determined by the type of brewer used based on sampled data. The brewer specifications allow for a soak time 115 that pre-wets the grinds to saturate the coffee grounds and enhance flavor extraction. The soak time combined with the brew time determines the effective overall brew time used as an input to the coffee extraction model.

Figure 3B:
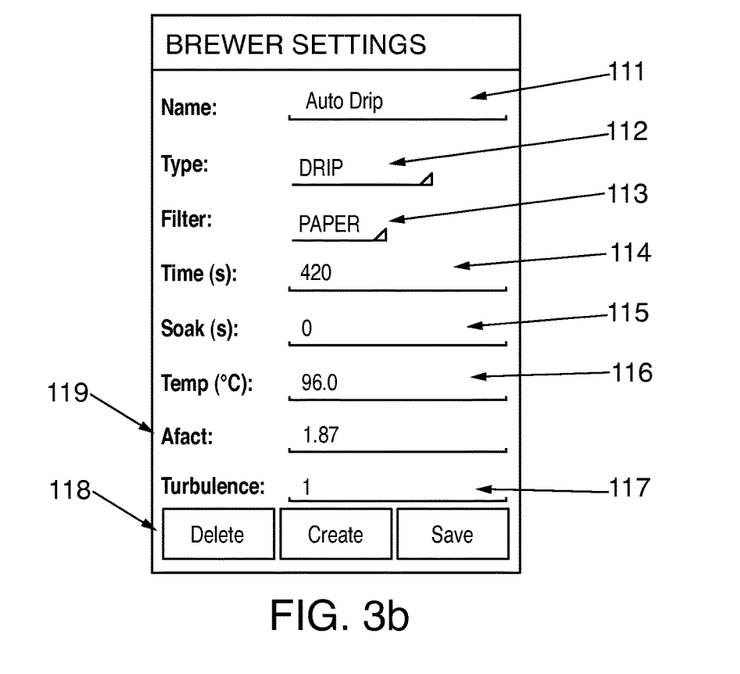
FIG. 3b is a depiction of another screen which may be displayed on the portable communications device of FIG. 2, the display showing brewer settings.

The type of brewer 112 determines if the brewer method is either percolation or immersion. Each brewer will have an absorption factor $A_F$ that defines how the extraction is processed in the brewer. The value of $A_F$ typically ranges from 0 to 3 and is set near 2 in the coffee brewer control chart shown in FIG. 1. For immersion type brewers, the value of $A_F$ is near 0 due to the water content within the absorption being at full extraction. The extraction yield is expressed by the following relation (formula 7):

$$EY = \frac{S}{1-S}(R - A_F)$$

where: S is the strength, R is the brew ratio and $A_F$ is the absorption factor 119 (See FIG. 3b). The strength is the same as TDS and the brew ratio is the proportion of water to coffee by weight. The percolation brewer method is a washed plus extraction process that leaves only a small amount of extracted product in the coffee bed while the immersion brewer method retains mostly the fully extracted brew in the coffee bed. Comparing each brew type at the same brew strength will result in lower strengths given the same extraction yield for the immersion brew relative to the percolation brew method and is reflected in the coffee model 214.

The primary contributor to predicting the coffee extraction is the mean grind size as expressed in formula (4). With a grind constant, k of 0.00923 and a mean grind size, d of 750 μm, the starting extraction, $E_0$ is reduced by 6.9 percent from the maximum extraction yield. Temperature and turbulence have an order of magnitude less influence on the resulting extraction. The following method determines the mean grind size, the most critical measurement that can be difficult to obtain accurately by any other cost effective method. This novel application uses image analysis to generate a particle distribution analysis of the grinds. The application includes a grind analyzer module as a built-in utility within the mobile application or provided as a computer or web-based application.

Image analysis is predicated on an image of actual particles of the ground coffee, the image taken prior to introducing water. This image is acquired by the camera of the smartphone, with a sampling of the ground coffee spread out on a suitable background of contrasting color, such as a white index card. The particles of ground coffee are separated from one another sufficiently so that the photographic image captures discrete particles.

Figure 5:
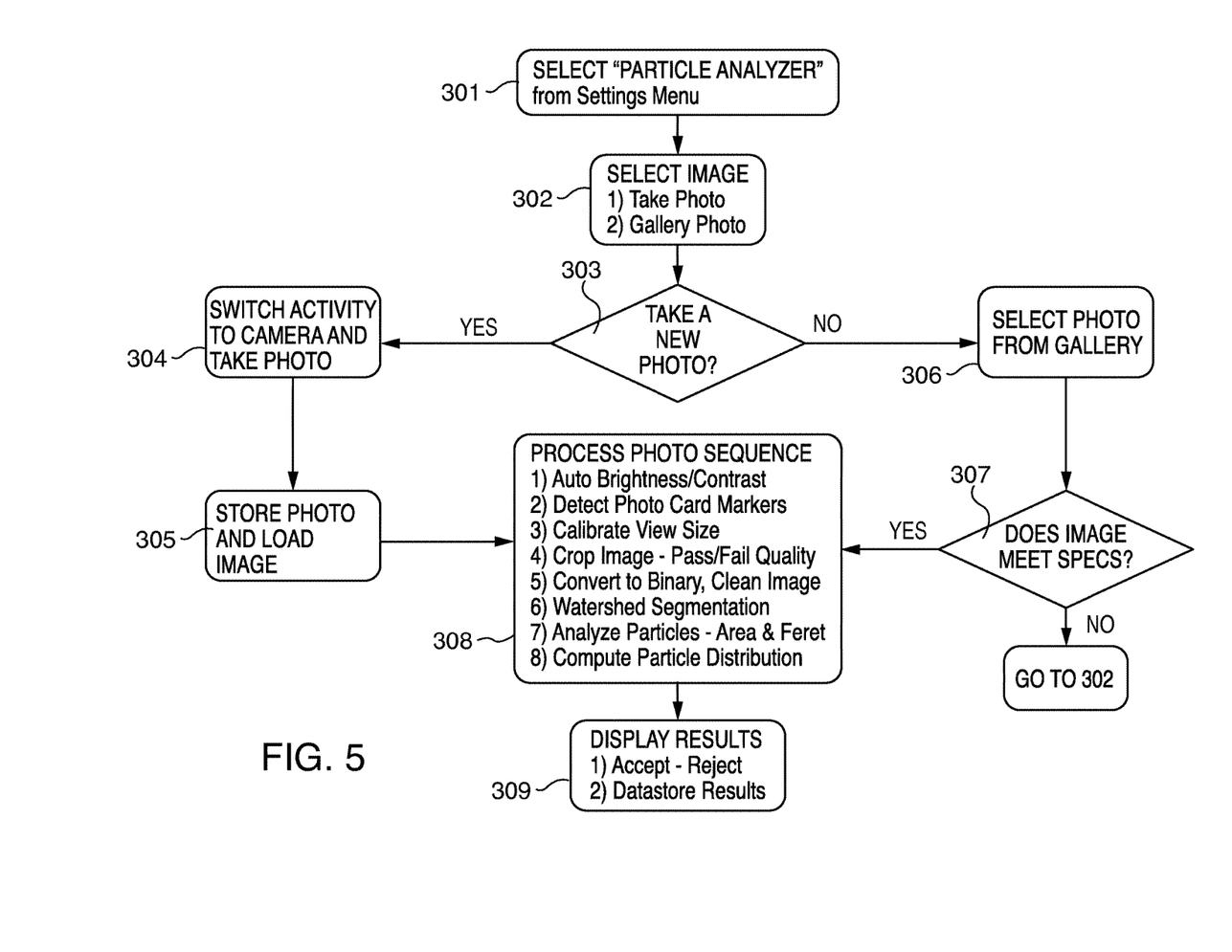
FIG. 5 is a flowchart of a process of analyzing particles using image analysis.

The procedure for using a coffee grind analyzer, a portion of the novel application, is shown as a flowchart in FIG. 5. Once the particle analyzer activity has started at 301 the user can either select an image 302 from the gallery or decide to take a new photo at 303. The analyzer specification 307 requires the use of a calibrated dispersion card that will determine the pixel units. Then the image analysis is conducted at 308 and proceeds through a sequence of methods that extract the particle outlines and computes a particle density distribution. The results are output to the display as a table or graph depending on user preference 309. Once completed and accepted, the data is stored in the local database for later retrieval.

The invention may be thought of as self-contained apparatus for predicting characteristics in a fluid into which comminuted solids are dispersed. The apparatus may be the smartphone described herein or may take the form of a tablet and other devices having the requisite features described herein. The portable data processing device may include the components shown in FIG. 2, for example.

Regardless of the specific form, the self-contained apparatus comprises a portable data processing device having a processor, having a memory in data transfer relation to the processor, and a camera in data transfer relation to the memory. The portable data processing device has a database loaded into the memory, including trait values for a plurality of candidate brewers and a plurality of candidate types of coffee. The portable data processing device has computer instructions loaded into the memory in a non-transitory computer-readable medium that when executed, are configured to instruct the processor to derive dimension values of the comminuted solids from images captured by the camera, and to enter the quantified dimensions into the memory as data for use in calculating the predictable characteristics of the fluid. The computer instructions further instruct the processor to utilize particle size characteristics of the comminuted solids taken from the dimension values and the trait values for the plurality of candidate substances to calculate predictable characteristics of the fluid after the particles are dispersed in the fluid.

As employed herein, candidate substances are different kinds of coffee, having been prepared in potentially a number of specific ways. These specific ways may encompass varieties of the coffee plant, roasting temperatures and times, ancillary treatments such as water based removal of caffeine, chemical flavorings or other additives, and the like.

The self-contained apparatus may also include a display on the portable communications device, and computer instructions embodied in a non-transitory computer-readable medium and loaded into the portable communications device that, when executed, are configured to instruct the data processor of the portable communications device to generate a data output from calculated predictable characteristics, and to display the data output on the display of the portable communications device in a format understandable by a person.

The outputs being displayed would include predicted characteristics of the prepared coffee. These would be presented in a format such as alphanumeric values, a bar or other type of graph, or other visual display understandable by a person.

The self-contained apparatus includes a user interface on the portable communications device, and computer instructions embodied in a non-transitory computer-readable medium that, when executed, are configured to instruct the portable communications device to receive, via the user interface of the self-contained apparatus, a rating set comprising the person's ratings for each of a plurality of rated items corresponding to the fluid into which comminuted solids are dispersed.

As employed herein, the ratings are preferences of an individual, such as the user of the novel system, or alternatively, as may be practiced in commercial settings, known preferences of a customer or supplier. Known preferences may be entered into the novel apparatus by personnel of a commercial establishment.

Figure 6:
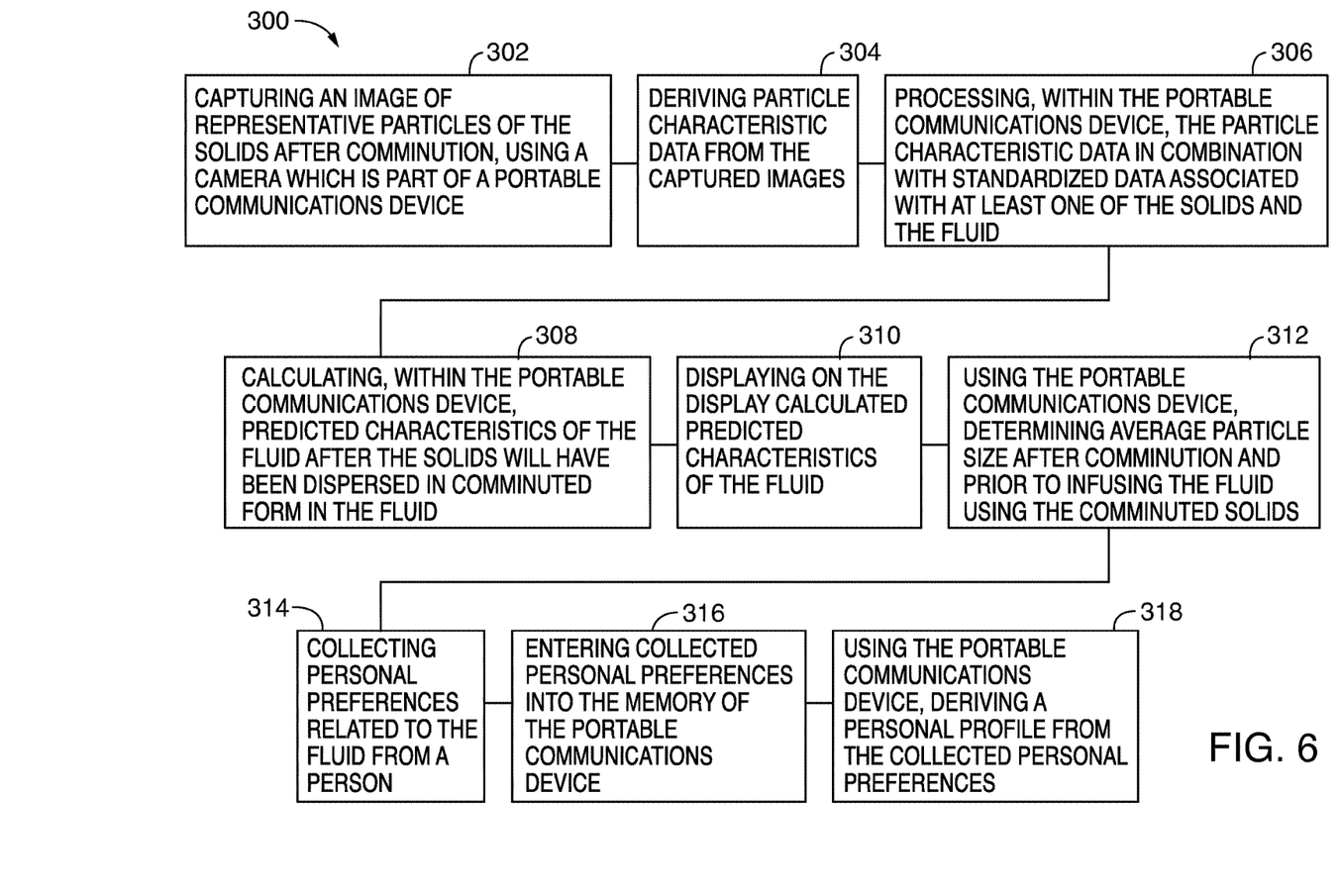
FIG. 6 is a block diagram of a method of predicting characteristics of a fluid into which solids are dispersed in comminuted form.

Referring to FIG. 6, the invention may be thought of as a method 300 for predicting characteristics of a fluid into which solids are dispersed in comminuted form, using a self-contained portable communications device.

The method 300 includes capturing an image of representative particles of the solids after comminution, using the camera which is part of the portable communications device (block 302). The method 300 includes deriving particle characteristic data from the captured images (block 304), and processing, within the portable communications device, the particle characteristic data in combination with known data associated with at least one of the solids and the fluid (block 306). The method 300 also includes calculating, within the portable communications device, predicted characteristics of the fluid after the solids will have been dispersed in comminuted form in the fluid (block 308).

Where the portable communications device includes a display, the method 300 may further include displaying on the display calculated predicted characteristics of the fluid (block 310).

Where deriving particle characteristic data from the captured images comprises using the portable communications device, the method 300 includes determining average particle size after comminution and prior to infusing the fluid using the comminuted solids (block 312).

The method 300 may further include collecting personal preferences related to the fluid for a person (block 314), entering collected personal preferences into the memory of the portable communications device (block 316), and, using the portable communications device, deriving a personal profile from the collected personal preferences (block 318). Personal preferences may be those of the person practicing the method 300. Alternatively, and again referring to the commercial setting, may have been previously collected, for example by surveys of customers. Previously collected personal preferences may be entered into the smartphone by personnel of a commercial establishment preparing coffee.

The personal profile may be stored in the memory and, for example, retrieved to prepare a single cup for a particular consumer. Alternatively, the personal profile may, for example, be transmitted to a remote database to form the basis for determining consumer trends, planning of future coffee offerings by a commercial establishment, planning of purchases of coffee supplies, and the like.

Figure 7A:
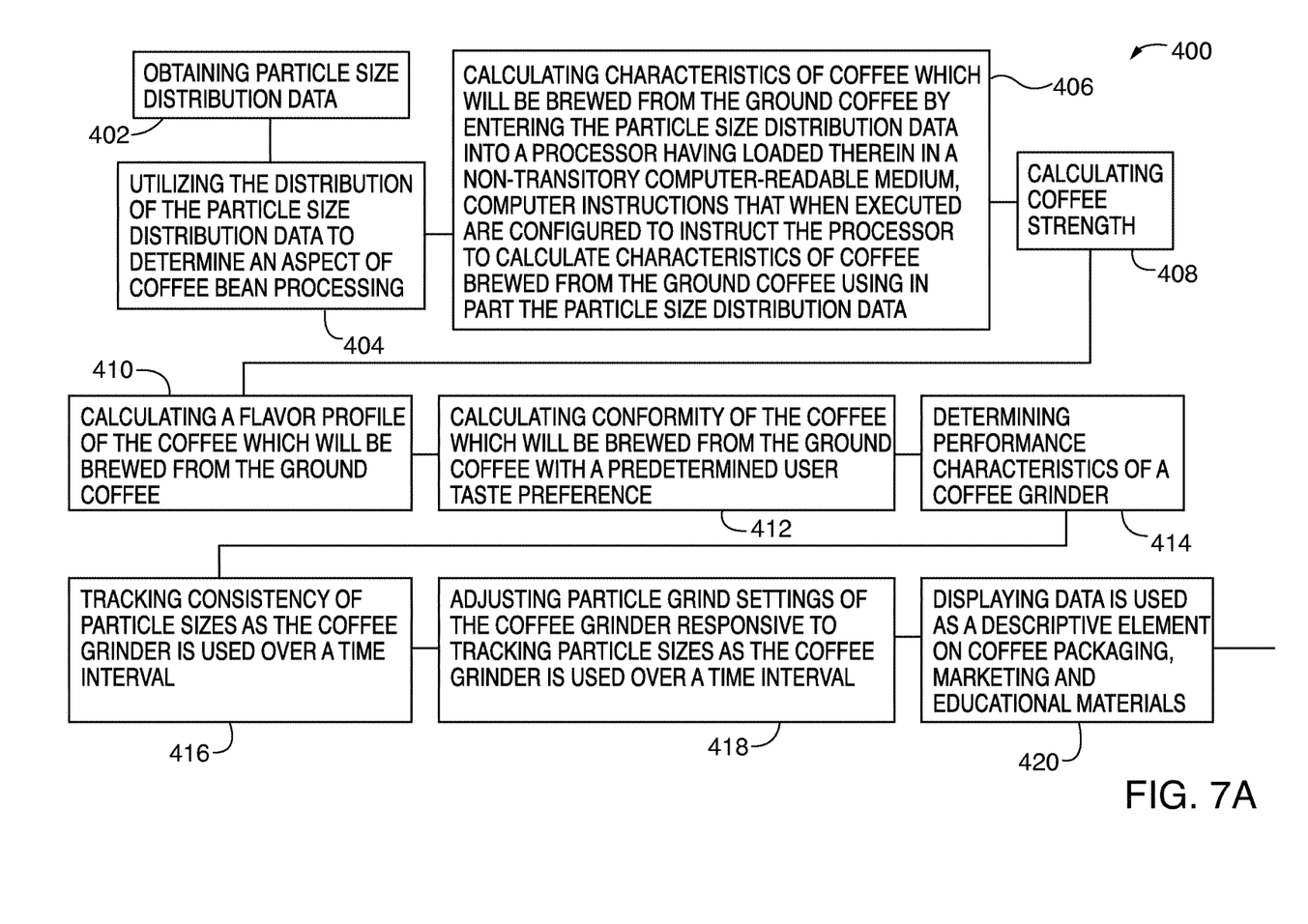
FIG. 7A is part of a block diagram of a method of utilizing particle size distribution of particles of ground coffee.

Referring to FIG. 7A, the invention may be thought of as a method 400 of utilizing particle size distribution of particles of ground coffee. The method 400 may use a self-contained portable communications device, utilizes the procedures and methods described herein. The method 400 includes obtaining particle size distribution data (block 402), and utilizing the particle size distribution data to determine an aspect of coffee bean processing (block 404). Coffee bean processing will be understood to encompass both brewing of the final beverage, and also preparation and commercial distribution of ground coffee. Utilizing the particle size distribution data will be understood to include such data in calculations. Calculations may be predictive of brewed coffee, or may be settings of coffee grinders, and control inputs to the brewing process, such as brewing times, amount of water to be used, and the like. Obtaining particle size distribution data may utilize the camera and image analysis presented herein, or may utilize other ways of gathering the particle size distribution data.

The method 400 may include calculating characteristics of coffee which will be brewed from the ground coffee by entering the particle size distribution data into a processor having loaded therein in a non-transitory computer-readable medium, computer instructions that when executed are configured to instruct the processor to calculate characteristics of coffee brewed from the ground coffee using in part the particle size distribution data (block 406).

In the method 400, calculating characteristics of coffee which will be brewed from the ground coffee may further comprise calculating coffee strength (block 408).

In the method 400, calculating characteristics of coffee which will be brewed from the ground coffee may further comprise calculating a flavor profile of the coffee which will be brewed from the ground coffee (block 410). This profile may be stored for subsequent retrieval and brewing of coffee to taste for one or more people. In commercial settings, profiles may be monitored for popularity, with future offerings being based on taste trends and other data taken from the profile or profiles.

In the method 400, calculating characteristics of coffee which will be brewed from the ground coffee may further comprise calculating conformity of the coffee which will be brewed from the ground coffee with a predetermined user taste preference (block 412).

In the method 400, analyzing the distribution of the particle size distribution data to determine an aspect of coffee bean processing may further comprise determining performance characteristics of a coffee grinder (block 414). Performance characteristics may be mapped to particular makes and models of coffee grinders, so that any coffee grinder of a plurality of different coffee grinder models may have its settings set to produce coffee of predetermined characteristics. Alternatively stated, a consistent coffee beverage may be easily obtained regardless of which of several available coffee grinders is used to grind coffee beans.

In the method 400, determining performance characteristics of a coffee grinder may further comprise tracking consistency of particle sizes as the coffee grinder is used over a time interval (block 416). This information may be used to assure proper operation of a coffee grinder. The information may also be used in establishing settings for other coffee grinders of the same make and model.

The method 400 may further comprise adjusting particle grind settings of the coffee grinder responsive to tracking particle sizes as the coffee grinder is used over a time interval (block 418). Should performance characteristics of a coffee grinder change, the coffee grinder may be adjusted to maintain a consistent product.

Figure 7B:
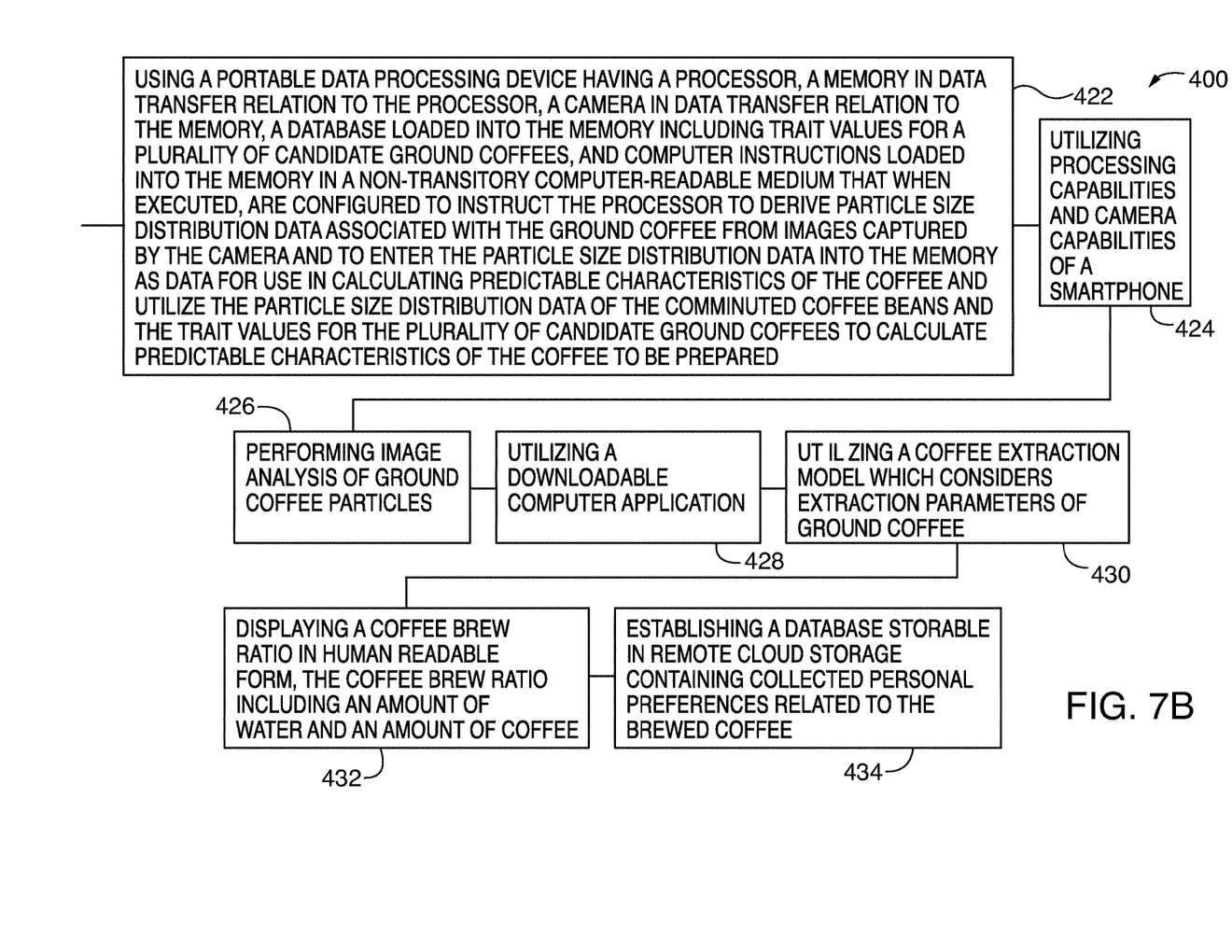
FIG. 7B is a complementing part of the block diagram of utilizing particle size distribution of particles of ground coffee.

The method 400 may further comprise displaying data corresponding to the particle grind size distribution data utilized as a descriptive element on coffee packaging, marketing and educational materials. (shown in part in block 420). This information may be used by a person at the time coffee is brewed, so that an accurately predicted coffee profile is produced in the subsequently brewed coffee.

In the method 400, obtaining the particle size distribution data may comprise using a portable data processing device having a processor, a memory in data transfer relation to the processor, and a camera in data transfer relation to the memory. The method 400 may comprise using a database loaded into the memory including trait values for a plurality of candidate ground coffees. The method 400 may comprise using computer instructions loaded into the memory in a non-transitory computer-readable medium that when executed, are configured to instruct the processor to derive particle size distribution data associated with the ground coffee from images captured by the camera and to enter the particle size distribution data into the memory as data for use in calculating predictable characteristics of the coffee, and utilize the particle size distribution data of the comminuted coffee beans and the trait values for the plurality of candidate ground coffees to calculate predictable characteristics of the coffee to be prepared (block 422). Using the portable apparatus makes producing coffee of predictable characteristics dependent upon only one physical monitoring or predicting device. Also, a general purpose communications device, such as the smartphone, may be utilized, thereby overcoming any necessity of providing a dedicated apparatus.

The method 400 may comprise utilizing processing capabilities and camera capabilities of a smartphone (block 424). A smartphone is one of the most practical forms of portable communications devices which may contain and process the application.

In the method 400, obtaining the particle size distribution data may comprise performing image analysis of ground coffee particles (block 426). Image analysis enables the actual ground coffee to be used for brewing to be used to acquire raw data regarding particle size distribution.

In the method 400, obtaining the particle size distribution data comprises utilizing a downloadable computer application (block 428). Using a downloadable computer application enables an electronic device intended for other purposes to serve as a platform for running the application.

In the method 400, determining an aspect of coffee bean processing may comprise utilizing a coffee extraction model which considers extraction parameters of ground coffee (block 430). Accuracy of predictions is increased over prior art methods when considering extraction parameters.

The method 400 may further comprise displaying a coffee brew ratio in human readable form, the coffee brew ratio including an amount of water and an amount of coffee (block 432). Display of the brew ratio enables expeditious setting of coffee brewing apparatus, with predictable results being readily achieved in the brewed coffee.

The method 400 may further comprise establishing a database storable in remote cloud storage containing collected personal preferences related to the brewed coffee (block 434). This enables a centralized database to store and enable retrieval of personal preferences from one location, and may distribute that personal preference to any commercial or other coffee brewing facility. For example, a patron of a chain of coffee brewing facilities may order his or her customized beverage from any outlet of the chain, relying on availability of his or her preferences from the centralized database.

It should be noted that the methods 300 and 400 need not be practiced utilizing all of the procedures shown in FIGS. 6 and 7. Rather, only the subject matter of blocks deemed appropriate for any particular application of the methods 300 and 400 may be utilized. Also, subject matter of the blocks need not necessarily be practiced in the order shown. The order of utilizing the subject matter of the blocks may be modified to suit any particular application of the methods 300 and 400, as is feasible.

While the present invention has been described in connection with what is considered the most practical and preferred embodiment, it is to be understood that the present invention is not to be limited to the disclosed arrangements, but is intended to cover various arrangements which are included within the spirit and scope of the broadest possible interpretation of the appended claims so as to encompass all modifications and equivalent arrangements which are possible.

I claim:

1. A method for predicting characteristics of coffee, using a self-contained portable communications device, the method comprising:
   capturing an image of ground coffee particles using a camera which is part of a portable communications device;
   deriving particle size distribution data from the captured image or images;
   processing, within the portable communications device, the particle size distribution data in combination with standardized data associated with the ground coffee particles; and
   calculating, within the portable communications device, predicted characteristics of the coffee after the ground coffee particles will have been extracted into water, the predicted characteristics of the coffee being based on at least the particle size distribution data of the ground coffee particles.

2. The method of claim 1, wherein the portable communications device includes a display, further comprising displaying on the display the predicted characteristics of the coffee.

3. The method of claim 1, wherein deriving the particle size distribution data from the captured images comprises, using the portable communications device, determining average particle size of the ground coffee particles prior to infusing the water with the ground coffee particles.

4. The method of claim 1, further comprising collecting personal preferences related to the coffee from a person, entering collected personal preferences into the memory of the portable communications device, and using the portable communications device, deriving a personal profile from the collected personal preferences.

5. Apparatus for predicting characteristics of coffee to be prepared from ground coffee particles, the apparatus comprising:

a communications device having a processor, a memory in data transfer relation to the processor, and a camera in data transfer relation to the memory;

a database loaded into the memory including trait values for a plurality of candidate brewing apparatus and trait values for a plurality of candidate coffee types; and computer instructions loaded into the memory in a non-transitory computer-readable medium that when executed, are configured to instruct the processor to derive particle size distribution data associated with the ground coffee particles from images captured by the camera and to enter the particle size distribution data into the memory as data for use in calculating predictable characteristics of the coffee, and utilize the particle size distribution data of the ground coffee particles and the trait values for the plurality of candidate brewing apparatus and trait values for a plurality of candidate coffee types to calculate an amount of coffee extraction from a brewing process utilizing the ground coffee particles.

6. The apparatus of claim 5, further comprising a display on the communications device and computer instructions embodied in a non-transitory computer-readable medium and loaded into communications device that, when executed, are configured to instruct the data processor of the communications device to generate a data output from calculated coffee extraction, and to display the data output on the display of the communications device in a format understandable by a person.

7. The apparatus of claim 5, further comprising a user interface on the communications device, and computer instructions embodied in a non-transitory computer-readable medium that, when executed, are configured to instruct the communications device to receive, via the user interface of the self-contained apparatus, a rating set comprising the person's ratings for each of a plurality of rated items corresponding to the coffee in which ground coffee particles are extracted.

8. A method of utilizing particle size distribution of ground coffee particles, comprising:
capturing an image of representative ground coffee particles using a camera which is part of a communications device;
obtaining particle size distribution data from the captured images; and
utilizing the distribution of the particle size distribution data to determine an amount of coffee extraction from a brewing process utilizing selected ground coffee particles.

9. The method of claim 8, further including calculating characteristics of coffee which will be brewed from the ground coffee particles by entering the particle size distribution data into a processor having loaded therein in a non-transitory computer-readable medium, computer instructions that when executed are configured to instruct the processor to calculate characteristics of coffee brewed from the ground coffee particles using in part the particle size distribution data.

10. The method of claim 9, wherein calculating characteristics of coffee which will be brewed from the ground coffee particles further comprises calculating and displaying a coffee to water ratio for a selected brewing device.

11. The method of claim 9, further comprising calculating conformity of the coffee which will be brewed from the ground coffee particles with a predetermined user taste preference.

12. The method of claim 8, wherein the particle size distribution relates to the flavor profile of the brewed coffee.

13. The method of claim 8, wherein analyzing the distribution of the particle size distribution data to determine an aspect of ground coffee particles further comprises determining performance characteristics of a coffee grinder.

14. The method of claim 13, wherein determining performance characteristics of a coffee grinder further comprises tracking consistency of particle sizes as the coffee grinder is used over a time interval.

15. The method of claim 13, further comprising using particle size distribution data as a means to calibrate a coffee grinder.

16. The method of claim 8, further comprising displaying data corresponding to the particle grind size distribution data utilized as a descriptive element on coffee packaging, marketing and educational materials.

17. The method of claim 8, wherein obtaining the particle size distribution data comprises using: a portable data processing device having a processor, a memory in data transfer relation to the processor, and a camera in data transfer relation to the memory, a database loaded into the memory including trait values for a plurality of candidate ground coffees, and computer instructions loaded into the memory in a non-transitory computer-readable medium that when executed, are configured to instruct the processor to derive particle size distribution data associated with the ground coffee particles from images captured by the camera and to enter the particle size distribution data into the memory as data for use in calculating an amount of coffee extraction from a brewing process utilizing selected ground coffee particles, and utilize the particle size distribution data of the ground coffee particles and trait values for a plurality of candidate coffee types to calculate the amount of coffee extraction for the coffee to be prepared.

18. The method of claim 17, further comprising utilizing processing capabilities and camera capabilities of a smartphone.

19. The method of claim 8, wherein obtaining the particle size distribution data comprises performing image analysis of ground coffee particles.

20. The method of claim 8, further including utilizing a coffee extraction model which considers extraction parameters of ground coffee particles.

21. A method for determining a coffee brew ratio utilizing a coffee extraction model that is configurable for a plurality of brewing apparatus, comprising
selecting a brewing method configured for said brewing apparatus that includes extraction parameters of said coffee extraction model;
determining the average grind size of the coffee grounds used in said coffee extraction model that is proportional to the average surface area of the coffee grounds, the determination of average grind size of the coffee grounds occurring prior to brewing coffee utilizing the coffee grounds, wherein the average grind size of the coffee grounds is determined using an image of the coffee grounds captured using a camera associated with a communication device; and,
computing the brew ratio given said average grind size and an adjustable desired coffee strength, which is equivalent to the percent of dissolved solids within the brewed coffee, the computing step being accomplished prior to brewing coffee utilizing the coffee grounds;
whereby, the coffee brew ratio is displayed in a human readable form as an amount of coffee and an amount of water with a plurality of measurement units.

22. A machine for determining the coffee brew ratio that results from a selected coffee brew strength using a plurality of brewing apparatus, comprising:

- a computer or derivative of, such as a tablet or a smartphone, which provides the framework for hosting the software application;
- a non-volatile memory in said computer that stores said software application that can be launched to begin execution and linked to associated databases;
- a user interface generated from said software application and presented on the computer display screen;
- an input device used to navigate said user interface in a plurality of form factors including but not limited to a touch screen or mechanical mouse;
- a plurality of widgets attached to said user interface that allow setting of values to be stored in said memory and/or database for use by a coffee extraction model that computes said coffee brew ratio;
- the software application being capable of determining the average grind size of the coffee grounds used in said coffee extraction model that is proportional to the average surface area of the sample coffee grounds, the software application being further capable of determining the average grind size of the coffee grounds prior to brewing coffee utilizing the coffee grounds, the average grind size being determined using an image of the coffee grounds captured using a camera associated with the machine; and,
- a grind size widget that is attached to said user interface that inputs said average grind size that is stored in said memory and accessed by said coffee extraction model;

whereby, the coffee brew ratio is displayed in a human readable form as an amount of coffee and an amount of water with a plurality of measurement units.

* * * * *